June 24, 1952 C. N. HASTIE, JR Plant Pat. 1,107
CAMELLIA PLANT
Filed July 25, 1949
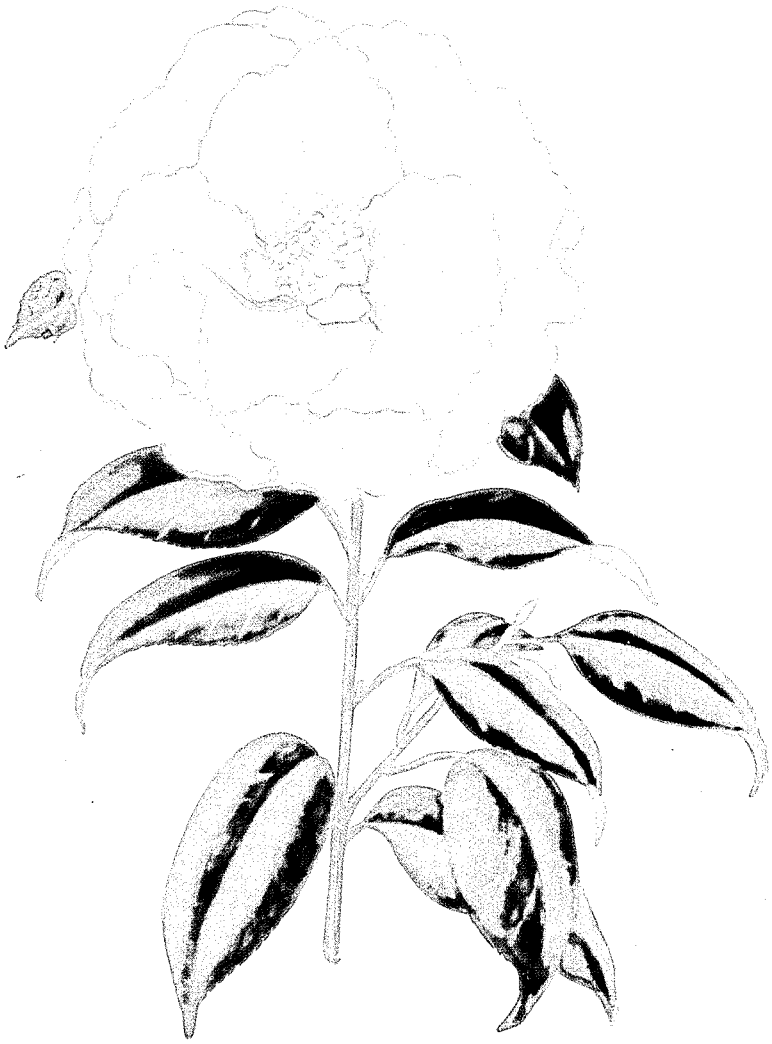
*INVENTOR.*
CARLISLE NORWOOD HASTIE, JR
*BY*
Cushman, Darby & Cushman
ATTORNEYS Patented June 24, 1952

Plant Pat. 1,107

UNITED STATES PATENT OFFICE 1,107

CAMELLIA PLANT

Carlisle Norwood Hastie, Jr., Charleston, S. C.

Application July 25, 1949, Serial No. 106,715

1 Claim. (Cl. 47—60)

The present invention relates to a new and distinct type of the camellia japonica of the variety "Troubadour" not a patented variety, the original "Troubadour" being an old camellia japonica growing in Magnolia Gardens, at Charleston, South Carolina. The deviation from types forming the subject matter of this invention originated as a sport on a plant of the "Troubadour," a variety growing in applicant's Magnolia Gardens and Nurseries, Charleston County, South Carolina, and exhibited flower, leaf, twig, and stem characteristics which distinguished it markedly from the parent, namely, the "Troubadour" variety of camellia japonica.

The new sported branch was observed and marked for identification; and in the succeeding season, showed the same novel and distinguishing attributes. The recurrence established fixation of the mutant. Scions of this mutant were then grafted on understock growing in applicant's Magnolia Gardens and Nurseries, Charleston County, South Carolina, with the result that flowers, foliage, stem, and twigs were asexually reproduced, having the same novel features of the mutant and the new type was permanently fixed.

The illustration herewith, forming part of this disclosure, shows the plant with stems, twigs, and foliage, the flower in substantially full front view; and side views of the flower from different angles.

The new and unusual qualities of this new and asexually produced type reside in its vigorous, healthy, distinct growth habits. It presents a tall, open growth and has twigs which are relatively small in diameter, in comparison to other camellias, although strong and fully equal to the support of foliage and flowers. The foliage is Spinach Green according to Plate #960 of the Royal Horticultural Society color chart, the leaves being lanceolate and of smooth texture. They are approximately two and one-half (2½) cms. wide, and on the average, approximately nine (9) cms. long. The leaf is arched throughout its length in a graceful formation, and is slightly keeled in cross-section.

The flowers show an outstanding departure from those of the parent, being semi-double and exhibiting in the average flower, from fourteen (14) to twenty (20) petals which are of wavy form and generally creped. These petals are further characterized and distinguished from those of other varieties by their texture, so that the flower resulting from this asexual reproduction is appreciably lighter in weight than other camellias of the same or comparable size, and danger of dropping or twig bending under flower weight is eliminated or largely reduced. In diameter, the flowers average four and one-half (4½) to five (5) inches and are geranium lake in color, according to Plate No. 20/2 of the horticultural color chart of the Royal Horticultural Society, shading slightly from the point of attachment at the calyx to the outer fringe of the petals. The stamens and their appendages are strong and erect, the pistils terminating in anthers which are yellowish or golden in color, contrasting effectively to the geranium lake color of the flowers.

The plant herein described is characterized by prolific quantity, size, and light weight of its flowers; their unique and distinctive coloring; the shape and coloring of its leaves; its sturdy, open, tall growth; its vigorous blooming habits, and particularly, the lasting quality of the cut flowers.

The following is a detailed description of the new variety, all color terminology being in accordance with the Royal Horticultural Society color chart.

Fragrance: None.

Buds: Sessile.

*Before calyx breaks.*—Size—medium.

*Form.*—Long, pointed.

*Sepals.*—Imbricated, broadly ovate in outline. Characterized by notch at tip instead of the usual point.

*Color.*—Fern Green at base to Lettuce Green at tip, according to color charts of Royal Horticultural Society.

*As bud opens.*—Petals of flower tend to project through apex of bud about ⅛'' before flower really opens up.

Time of blooming: Middle of January through end of February.

Color of flower: Geranium Lake in color, according to Plate No. 20/2 of the horticultural color chart of the Royal Horticultural Society, shading slightly to Color No. 20/3 from point of attachment at the calyx to the outer fringe of the petals.

Bloom: *Size.*—4½ to 5 inches in diameter when fully open.

*Petalage.*—Semi-double, according to classification of the American Camellia Society. Arranged regularly.

*Form.*—Regular semi-double, 14 to 20 petals.

Petals: Thin texture, with inside and outside satiny. *Shape.*—Obovate, with creped edges. Wavy form.

Leaf: Spinach Green—Plate #960 of Royal Horticultural Society color chart.

Having disclosed my invention, I claim:

The new and distinct variety of plant of the species camellia japonica of the Troubadour type, substantially as described and illustrated, characterized by its tall, open growth; its slender twigs; prolific flowering habit; its dark green lanceolate leaves; the distinctive semi-double form and coloring of its flowers; their wavy generally creped petals, and lasting qualities of the cut flowers.

CARLISLE NORWOOD HASTIE, JR.

REFERENCES CITED

The following references are of record in the file of this patent:

UNITED STATES PATENTS

| Number | Name | Date |
|---|---|---|
| Pl. Pt. 589 | Robinson | June 8, 1943 |
| Pl. Pt. 891 | Armstrong | Nov. 8, 1949 |
| Pl. Pt. 907 | Armstrong | Dec. 20, 1949 |
| Pl. Pt. 927 | Pfingstl | Mar. 21, 1950 |